US007232656B2

(12) United States Patent
Balasubramanian et al.

(10) Patent No.: US 7,232,656 B2
(45) Date of Patent: *Jun. 19, 2007

(54) ARRAYED BIOMOLECULES AND THEIR USE IN SEQUENCING

(75) Inventors: Shankar Balasubramanian, Waldon (GB); David Klenerman, Waldon (GB); Colin Barnes, Waldon (GB); Mark Allen Osborne, Waldon (GB)

(73) Assignee: Solexa Ltd., Essex (GB)

( * ) Notice: Subject to any disclaimer, the term of this patent is extended or adjusted under 35 U.S.C. 154(b) by 427 days.

This patent is subject to a terminal disclaimer.

(21) Appl. No.: 10/610,305

(22) Filed: Jun. 30, 2003

(65) Prior Publication Data

US 2004/0091903 A1    May 13, 2004

Related U.S. Application Data

(63) Continuation of application No. 09/771,708, filed on Jan. 30, 2001, now Pat. No. 6,787,308, which is a continuation-in-part of application No. PCT/GB99/02487, filed on Jul. 30, 1999.

(30) Foreign Application Priority Data

| Jul. 30, 1998 | (EP) | 98306094 |
| Oct. 16, 1998 | (GB) | 9822670.7 |
| Feb. 1, 2000 | (GB) | 0002310.1 |

(51) Int. Cl.
   *C12Q 1/68*   (2006.01)
   *C07H 21/02*  (2006.01)
   *C07H 21/04*  (2006.01)

(52) U.S. Cl. .................... 435/6; 536/23.1; 536/24.3

(58) Field of Classification Search .................... 435/6; 536/23.1, 24.3
   See application file for complete search history.

(56) References Cited

U.S. PATENT DOCUMENTS

| 5,302,509 A | 4/1994 | Cheeseman |
| 5,314,829 A | 5/1994 | Coles |
| 5,634,413 A | 6/1997 | Listner et al. |
| 5,643,768 A | 7/1997 | Kawasaki |
| 5,658,736 A * | 8/1997 | Wong ............................. 435/6 |
| 5,658,754 A | 8/1997 | Kawasaki |
| 5,709,999 A * | 1/1998 | Shattuck-Eidens et al. .... 435/6 |
| 5,780,231 A | 7/1998 | Brenner |

FOREIGN PATENT DOCUMENTS

| DE | 196 12 356 A1 | 10/1997 |
| EP | 0 665 293 A2 | 8/1995 |
| EP | 0 721 016 A2 | 7/1996 |
| EP | 0 853 129 A2 | 7/1998 |
| EP | 0 995 804 A2 | 4/2000 |
| WO | WO 89/03432 | 4/1989 |
| WO | WO 90/13666 | 11/1990 |
| WO | WO 93/21340 | 10/1993 |
| WO | WO 95/20053 | 7/1995 |
| WO | WO 96/27025 | * 9/1996 |
| WO | WO 96/36731 | 11/1996 |
| WO | WO 97/04131 | 2/1997 |
| WO | WO 97/08183 | 3/1997 |
| WO | WO 98/03673 | 1/1998 |
| WO | WO 98/20019 | 5/1998 |
| WO | WO 98/29376 | 7/1998 |
| WO | WO 99/05315 | 2/1999 |
| WO | WO 99/05321 | 2/1999 |
| WO | WO 99/28494 | 6/1999 |
| WO | WO 99/28505 | 6/1999 |

OTHER PUBLICATIONS

Pastinen et al., "Minisequencing: A Specific Tool for DNA Analysis and Diagnostics on Oligonucleotide Arrays," Genome Research, Jun. 1997, vol. 7, No. 6, pp. 606-614).*
Ronaghi et al., "PCR-Introduced Loop Structure as Primer in DNA Sequencing," Biotechniques, Nov. 1998, vol. 25, pp. 876-884.*
2003 Release: International Consortium Completes HGP; International Consortium Completes Human Genome Project; pp. 1-7; Apr. 14, 2003.
CNN.com; Genome announcement a milestone, but only a beginning; pp. 1-6; Jun. 26, 2000.
S. Foder et al., "Combinatorial Chemistry—Applications of Light-Directed Chemical Synthesis", *Trends in Biotechnology*, Jan. 1994, vol. 12, pp. 19-26.
M. Schena et al., "Quantitative Monitoring of Gene Expression Patterns with a Complementary DNA Microarry", *SCIENCE*, Oct. 20, 1995, vol. 270, pp. 467-470.
S. Tyagi et al., "Molecular Beacons: Probes that Fluoresce Upon Hybridization", *Nature Biotechnology*, Mar. 1996, vol. 14, pp. 303-308.
M. Bulyk et al., "Quantifying DNA-Protein Interactions by Double-Stranded DNA Arrays", *Nature Biotechnology*, Jun. 1999, vol. 17, pp. 573-577.
R. Vale et al., "Direct Observation of Single Kinesin Molecules Moving Along Microtubules", *NATURE*, Apr. 1996, vol. 380, pp. 451-453.
P. Moyer et al., "Near-Field Optical Microscopes Break the Diffraction Limit", *Laser Focus World*, Oct. 1993, pp. 105-109.
H. Hansma et al., "Biomolecular Imaging with the Atomic Force Microscope", *Annu. Rev. Biophys. Biomol. Struct.*, 1994, vol. 23, pp. 115-139.
G. Binnig et al., "Scanning Tunneling Microscopy", *Helvetica Physica Acta*. vol. 55, 1982, pp. 726-735.
A. Mirzabekov, "DNA Sequencing by Hybridization—A Megasequencing Method and a Diagnostic Tool?", *Trends in Biotechnology*, Jan. 1994, vol. 12, pp. 27-32.

* cited by examiner

*Primary Examiner*—Ethan Whisenant
(74) *Attorney, Agent, or Firm*—Klauber & Jackson

(57) ABSTRACT

The invention is directed to a method for analysing genome wide variation in an individual. The method comprises randomly fragmenting the individual's genome and generating sequence reads of multiple bases on all fragments of the individual's genome, aligning the sequence reads generated with a known genomic reference sequence, and analysing variations between the sequence reads derived from the individual's genome and the known genomic reference sequence.

9 Claims, 5 Drawing Sheets

FIG. 4A
FIG. 4B
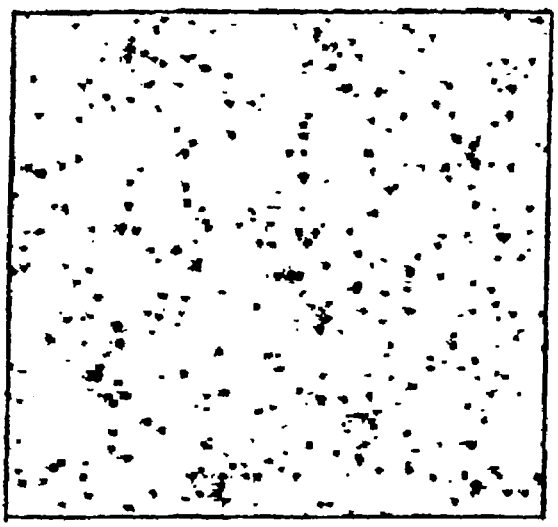
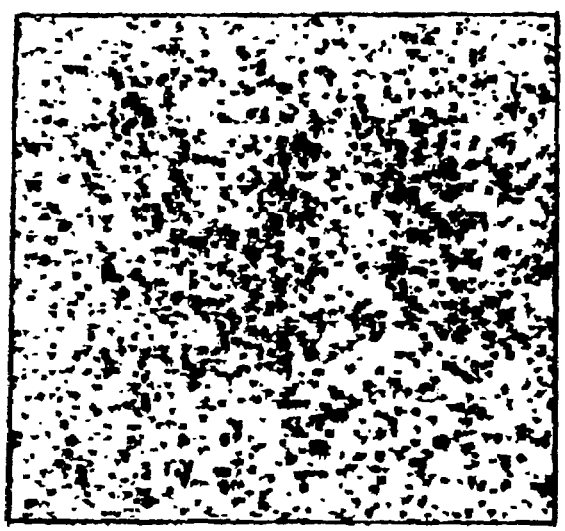
FIG. 4C

FIG. 5A
532/580 nm
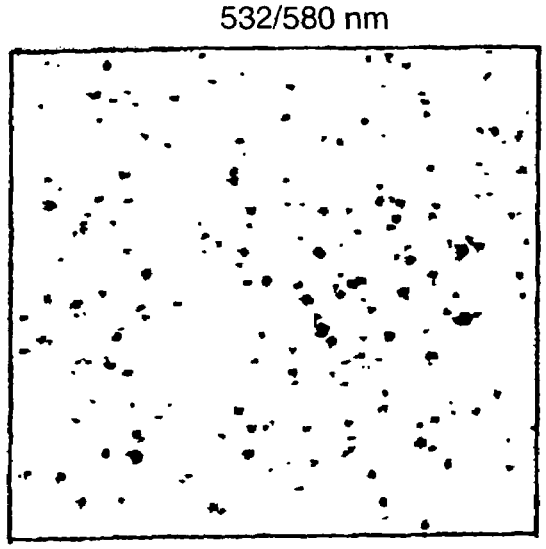
FIG. 5B
630/670 nm
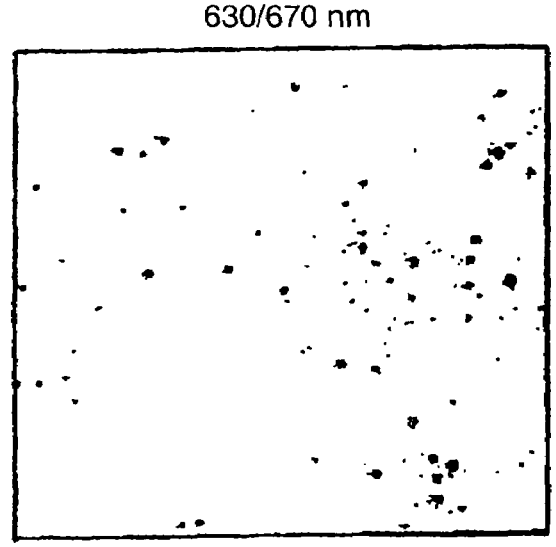
532/670 nm
FIG. 5C
580/670 nm
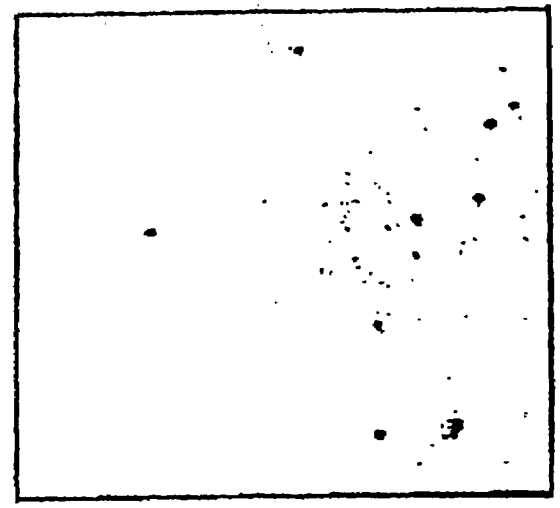
FIG. 5D

ARRAYED BIOMOLECULES AND THEIR USE IN SEQUENCING

CROSS REFERENCE TO RELATED APPLICATIONS

The present application is a Continuation of application Ser. No. 09/771,708 filed Jan. 30, 2001, now U.S. Pat. No. 6,787,308, issued Sep. 7, 2004, which is a continuation in part of International Application No. PCT/GB99/02487, which designated the United States and was filed on Jul. 30, 1999, was published in English, and which claims the benefit of British Application GB9822670.7, filed Oct. 16, 1998, and also claims benefit of European Application EP98306094.8, filed Jun. 30, 1998. The entire teachings of the above applications are incorporated herein by reference.

FIELD OF THE INVENTION

This invention relates to fabricated arrays of molecules, and to their analytical applications. In particular, this invention relates to the use of fabricated arrays in methods for obtaining genetic sequence information.

BACKGROUND OF THE INVENTION

Advances in the study of molecules have been led, in part, by improvement in technologies used to characterise the molecules or their biological reactions. In particular, the study of nucleic acids, DNA and RNA, has benefited from developing technologies used for sequence analysis and the study of hybridisation events.

An example of the technologies that have improved the study of nucleic acids, is the development of fabricated arrays of immobilised nucleic acids. These arrays typically consist of a high-density matrix of polynucleotides immobilized onto a solid support material Fodor et al., Trends in Biotechnology (1994) 12.19–26, describes ways of assembling the nucleic acid arrays using a chemically sensitised glass surface protected by a mask, but exposed at defined areas to allow attachment of suitably modified nucleotides. Typically, these arrays may be described as "many molecule" arrays, as distinct regions are formed on the solid support comprising a high density of one specific type of polynucleotide.

An alternative approach is described by Schena et al., Science (1995) 270.467–470, where samples of DNA are positioned at predetermined sites on a glass microscope slide by robotic micropipetting techniques. The DNA is attached to the glass surface along its entire length by non-covalent electrostatic interactions. However, although hybridisation with complementary DNA sequences can occur, this approach may not permit the DNA to be freely available for interacting with other components such as polymerase enzymes, DNA-binding proteins etc.

Recently, the Human Genome Project determined the entire sequence of the human genome-all $3 \times 10^9$ bases. The sequence information represents that of an average human. However, there is still considerable interest in identifying differences in the genetic sequence between different individuals. The most common form of genetic variation is single nucleotide polymorphisms (SNPs). On average one base in 1000 is a SNP, which means that there are 3 million SNPs for any individual. Some of the SNPs are in coding regions and produce proteins with different binding affinities or properties. Some are in regulatory regions and result in a different response to changes in levels of metabolites or messengers. SNPs are also found in noncoding regions, and these are also important as they may correlate with SNPs in coding or regulatory regions. The key problem is to develop a low cost way of determining one or more of the SNPs for an individual.

The nucleic acid arrays may be used to determine SNPs, and they have been used to study hybridisation events (Mirzabekov, Trends in Biotechnology (1994) 12.27–32). Many of these hybidisation events are detected using fluorescent labels attached to nucleotides, the labels being detected using a sensitive fluorescent detector, e.g. a charge-coupled detector (CCD). The major disadvantages of these methods are that it is not possible to sequence long stretches of DNA, and that repeat sequences can lead to ambiguity in the results. These problems are recognised in Automation Technologies for Genome Characterisation, Wiley-Interscience (1997), ed T J Beugelsdijk, Chapter 10 205–225.

In addition, the use of high-density arrays in a multi-step analysis procedure can lead to problems with phasing. Phasing problems result from a loss in the synchronisation of a reaction step occurring on different molecules of the array. If some of the arrayed molecules fail to undergo a step in the procedure, subsequent results obtained for these molecules will no longer be in step with results obtained for the other arrayed molecules. The proportion of molecules out of phase will increase through successive steps and consequently the results detected will become ambiguous. This problem is recognized in the sequencing procedure described in U.S. Pat. No. 5,302,509.

An alternative sequencing approach is disclosed in EP-A-0381693, which comprises hybridising a fluorescently-labelled strand of DNA to a target DNA sample suspended in a flowing sample stream, and then using an exonuclease to cleave repeatedly the end base from the hybridised DNA. The cleaved bases are detected in sequential passage through a detector, allowing reconstruction of the base sequence of the DNA. Each of the different nucleotides has a distinct fluorescent label attached which is detected by laser-induced fluorescence. This is a complex method, primarily because it is difficult to ensure that every nucleotide of the DNA strand is labelled and that this has been achieved with high fidelity to the original sequence.

WO-A-96/27025 is a general disclosure of single molecule arrays. Although sequencing procedures are disclosed, there is little description of the applications to which the arrays can be applied. There is also only a general discussion on how to prepare the arrays.

SUMMARY OF THE INVENTION

According to the present invention, a device comprises a high density array of molecules capable of interrogation and immobilised on a solid generally planar source, wherein the array allows the molecules to be individually resolved by optical microscopy, and wherein each molecule is immobilised by covalent bonding to the surface, other than at that part of each molecule that can be interrogated.

According to a second aspect of the invention, a device comprises a high density array of relatively short molecules and relatively long polynucleotides immobilised on the surface of a solid support, wherein the polynucleotides are at a density that permits individual resolution of those parts that extend beyond the relatively short molecules. In this aspect, the shorter molecules can prevent non-specific binding of reagents to the solid support, and therefore reduce background interference.

According to a third aspect of the invention, a device comprises an array of polynucleotide molecules immobilised on a solid surface, wherein each molecule comprises a polynucleotide duplex linked via a covalent bond to form a hairpin loop structure, one end of which comprises a target polynucleotide, and the array has a surface density which allows the target polynucleotides to be individually resolved. In this aspect, the hairpin structures act to tether the target to a primer polynucleotide. This prevents loss of the primer-target during the washing steps of a sequencing procedure. The hairpins may therefore improve the efficiency of the sequencing procedures.

The arrays of the present invention comprise what are effectively single molecules. This has many important benefits for the study of the molecules and their interaction with other biological molecules. In particular, fluorescence events occuring on each molecule can be detected using an optical microscope linked to a sensitive detector, resulting in a distinct signal for each molecule.

When used in a multi-step analysis of a population of single molecules, the phasing problems that are encountered using high density (multi-molecule) arrays of the prior art, can be reduced or removed. Therefore, the arrays also permit a massively parallel approach to monitoring fluorescent or other events on the molecules. Such massively parallel data acquisition makes the arrays extremely useful in a wide range of analysis procedures which involve the screening/ characterising of heterogeneous mixtures of molecules. The arrays can be used to characterise a particular synthetic chemical or biological moiety, for example in screening for particular molecules produced in combinatorial synthesis reactions.

The arrays of the present invention are particularly suitable for use with polynucleotides as the molecular species. The preparation of the arrays requires only small amounts of polynucleotide sample and other reagents, and can be carried out by simple means. Polynucleotide arrays according to the invention permit massively parallel sequencing chemistries to be performed. For example, the arrays permit simultaneous chemical reactions on and analysis of many individual polynucleotide molecules. The arrays are therefore very suitable for determining polynucleotide sequences.

An array of the invention may also be used to generate a spatial addressable array of single polynucleotide molecules. This is the simple consequence of sequencing the array. Particular advantages of such a spatially addressable array include the following.

1) Polynucleotide molecules on the array may act as identifier tags and may only need to be 10–20 bases long, and the efficiency required in the sequencing steps may only need to be better than 50%, as there will be no phasing problems.

2) The arrays may be reusable for screening once created and sequenced. All possible sequences can be produced in a very simple way, e.g. compared to a high density multi-molecule DNA chip made using photolithography.

DESCRIPTION OF THE DRAWINGS

FIG. 4 shows fluorescently labelled single molecule DNA covalently attached to a solid surface, and FIG. 5 shows images of surface bound oligonucleotides hybridised with the complementary sequence.

DESCRIPTION OF THE INVENTION

Figure 1:
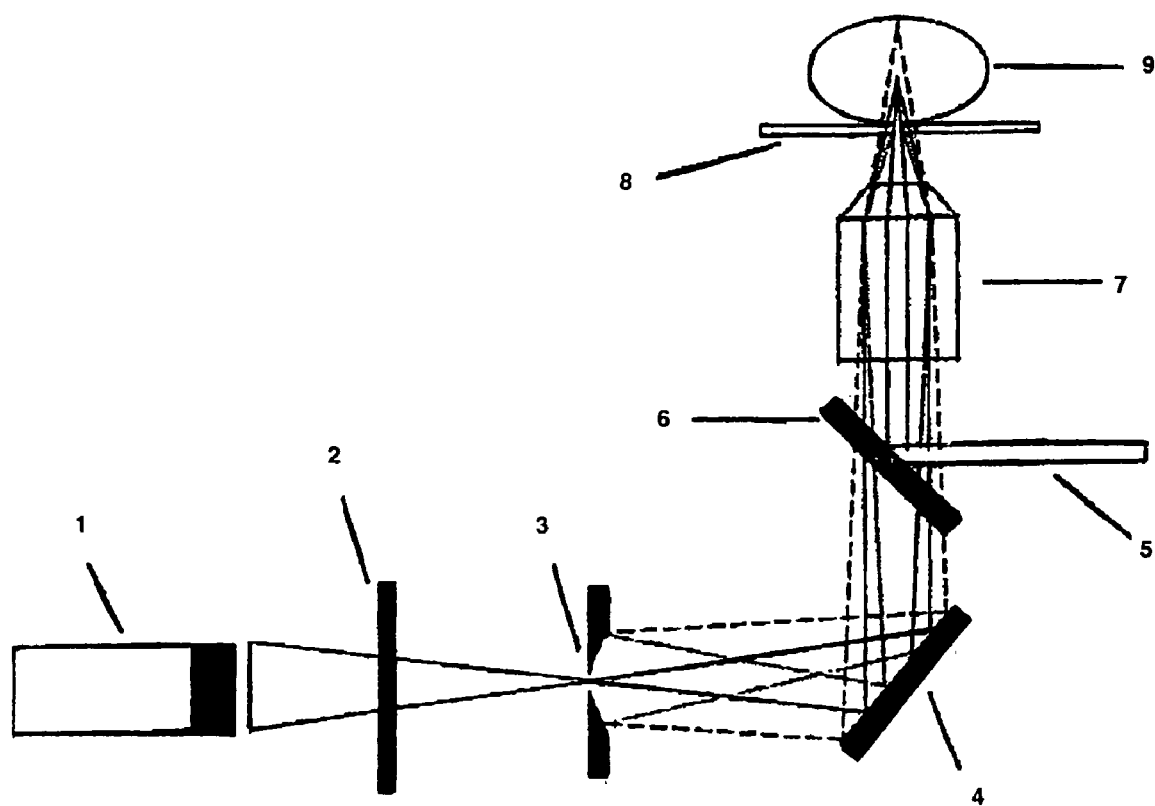
FIG. 1 is a schematic representation of apparatus that may be used to image arrays of the present invention.

According to the present invention, the single molecules immobilised onto the surface of a solid support should be capable of being resolved by optical means. This means that within the resolvable area of the particular imaging device used, there must be one or more distinct images each representing one molecule. Typically, the molecules of the array are resolved using a single molecule fluorescence microscope equipped with a sensitive detector, e.g. a charge-coupled detector (CCD). Each molecule of the array may be analysed simultaneously or, by scanning the array, a fist sequential analysis can be performed.

The molecules of the array are typically DNA, RNA or nucleic acid mimics, e.g. DNA or 2'-O-Meth-RNA. However, any other biomolecules, including peptides, polypeptides and other organic molecules, may be used. The molecules are formed on the array to allow interaction with other "cognate" molecules. It is therefore important to immobilise the molecules so that the portion of the molecule not physically attached to solid support is capable of being interrupted by a cognate. In some applications all the molecules in the single array will be the same, and may be used to interrogate molecules that are largely distinct. In other applications, the molecules on the array may all, or substantially all, be different, e.g. less than 50%, preferably less than 30% of the molecules will be the same.

The term "single molecule" is used herein to distinguish from high density multi-molecule arrays in the prior art, which may comprise distinct clusters of many molecules of the same type.

The term "individually resolved" is used herein to indicate that, when visualised, it is possible to distinguish one molecule on the array from its neighbouring molecules. Visualisation may be effected by the use of reporter labels, e.g. fluorophores, the signal of which is individually resolved.

The term "cognate molecule" is used herein to refer to any molecule capable of interacting, or interrogating, the arrayed molecule. The cognate may be a molecule that binds specifically to the arrayed molecule, for example a complementary polynucleotide, in a hybridisation reaction.

The term "interrogate" is used herein to refer to any interaction of the arrayed molecule with any other molecule. The interaction may be covalent or non-covalent.

The terms "arrayed polynucleotides" and "polynucleotide arrays" are used herein to define a plurality of single molecules that are characterised by comprising a polynucleotide. The term is intended to include the attachment of other molecules to a solid surface, the molecules having a polynucleotide attached that can be further interrogated. For example, the arrays may comprise protein molecules immobilised on a solid surface, the protein molecules being conjugated or otherwise bound to a short polynucleotide molecule that may be interrogated, to address the array.

The density of the arrays is not critical. However, the present invention can make use of a high density of single molecules, and these are preferable. For example, arrays with a density of $10^6$–$10^9$ molecules per $cm^2$ may be used. Preferably, the density is at least $10^7/cm^2$ and typically up to $10^8/cm^2$. These high density arrays are in contrast to other arrays which may be described in the art as "high density"

but which are not necessarily as high and/or which do not allow single molecule resolution.

Using the methods and apparatus of the present invention, it may be possible to image at least $10^7$ or $10^8$ molecules simultaneously. Fast sequential imaging may be achieved using a scanning apparatus; shifting and transfer between images may allow higher numbers of molecules to be imaged.

The extent of separation between the individual molecules on the array will be determined, in part, by the particular technique used to resolve the individual molecule. Apparatus used to image molecular arrays are known to those skilled in the art. For example, a confocal scanning microscope may be used to scan the surface of the array with a laser to image directly a fluorophore incorporated on the individual molecule by fluorescence. This may be achieved using the apparatus illustrated in FIG. 1, FIG. 1 shows a detector 1 at bandpass filter 2, a pinhole 3, a mirror 4 a laser beams 5 a dichroic mirror 6, an objective 7, a glass coverslip 8 and a sample 9 under study. Alternatively, a sensitive 2-D detector, such as a charge-coupled detector, can be used to provide a 2-D image representing the individual molecules on the array.

Resolving single molecules on the array with a 2-D detector can be done it at 100× magnification, adjacent molecules are separated by a distance of approximately at least 250 nm, preferably at least 300 nm and more preferably at least 350 nm. It will be appreciated that these distances are dependent on magnification, and flat other values can be determined accordingly, by one of ordinary skill in the art.

Other techniques such as scanning near-field optical microscopy (SNOM) are available which are capable of greater optical resolution, thereby permitting more dense arrays to be used. For example, using SNOM, adjacent molecules may be separated by a distance of less than 100 nm, e.g. 10 nm. For a description of scanning near-field optical microscopy, see Moyer et al, Laser Focus World (1993) 29(10).

An additional technique that may be used is surface-specific total internal reflection fluorescence microscopy (TIRFM); see, for example, Vale et al., Nature, (1996) 380. 451–453). Using this technique, it is possible to achieve wide-field imaging (up to 100 μm×100 μm) with single molecule sensitivity. This may allow arrays of greater than $10^7$ resolvable molecules per $cm^2$ to be used.

Additionally, the techniques of scanning tunnelling microscopy (Binnig et al, Helvetica Physica Acta (1982) 55:726–735) and atomic force microscopy (Hansma, Ann. Rev Biophys Biomol Struct (1994) 23 115–139) are suitable for imaging the arrays of the present invention. Other devices which do not rely on microscopy may also be used, provided that they are capable of imaging within discrete areas on a solid support.

Single molecules may be arrayed by immobilisation to the surface of a solid support. This may be carried out by any known technique, provided that suitable conditions are used to ensure adequate separation of the molecules. Generally the array is produced by dispensing small volumes of a sample containing a mixture of molecules onto a suitably prepared solid surface, or by applying a dilute solution to the solid surface to generate a random array. In this manner, a mixture of different molecules may be arrayed by simple means. The formation of the single molecule array then permits interrogation of each arrayed molecule to be carried out.

Suitable solid supports are available commercially, and will be apparent to the skilled person. The supports may be manufactured from materials such as glass, ceramics, silica and silicon. The supports usually comprise a flat (planar) surface, or at least an array in which the molecules to be interrogated are in the same plane. Any suitable size may be used. For example, the supports might be of the order of 1–10 cm in each direction.

It is important to prepare the solid support under conditions which minimise or avoid the presence of contaminants. The solid support must be cleaned thoroughly, preferably with a suitable detergent, e.g. Decon-90, to remove dust and other contaminants.

Immobilisation may be by specific covalent or non-covalent interactions. Covalent attachment is preferred. If the molecule is a polynucleotide, immobilisation will preferably be at either the 5' or 3' position so that the polynucleotide is attached to the solid support at one end only. However, the polynucleotide may be attached to the solid support at any position along its length, the attachment acting to tether the polynucleotide to the solid support. The immobilised polynucleotide is then able to undergo interactions with other molecules or cognates at positions distant from the solid support. Typically the interaction will be such that it is possible to remove any molecules bound to the solid support through non-specific interactions e.g. by washing. Immobilisation in this manner results in well separated single molecules. The advantage of this is that it prevents interaction between neighbouring molecules on the array, which may hinder interrogation of the array.

In one embodiment of the invention, the surface of a solid support is first coated with streptavidin or avidin, and then a dilute solution of a biotinylated molecule is added at discrete sites on the surface using, for example, a nanoliter dispenser to deliver one molecule on average to each site.

In a preferred embodiment of the invention, The solid surface is coated with an epoxide and the molecules are coupled via an amine linkage. It is also preferable to avoid or reduce salt present in the solution containing the molecule to be arrayed. Reducing the salt concentration minimises the possibility of the molecules aggregating in the solution, which may affect the positioning on the array.

If the molecule is a polynucleotide, then immobilisation may be via hybridisation to a complementary nucleic acid molecule previously attached to a solid support. For example, the surface of a solid support may be first coated with a primer polynucleotide at discrete sites on the surface. Single-stranded polynucleotides are then brought into contact with the arrayed primers under hybridising conditions and allowed to "self-sort" onto the array. In this way, the arrays may be used to separate the desired polynucleotides from a heterogeneous sample of polynucleotides.

Alternatively, the arrayed primers may be composed of double-stranded polynucleotides with a single-stranded overhang ("sticky-ends"). Hybridisation with target polynucleotides is then allowed to occur and a DNA ligase used to covalently link the target DNA to the primer. The second DNA strand can then be removed under melting conditions to leave an arrayed polynucleotide.

Figure 2:
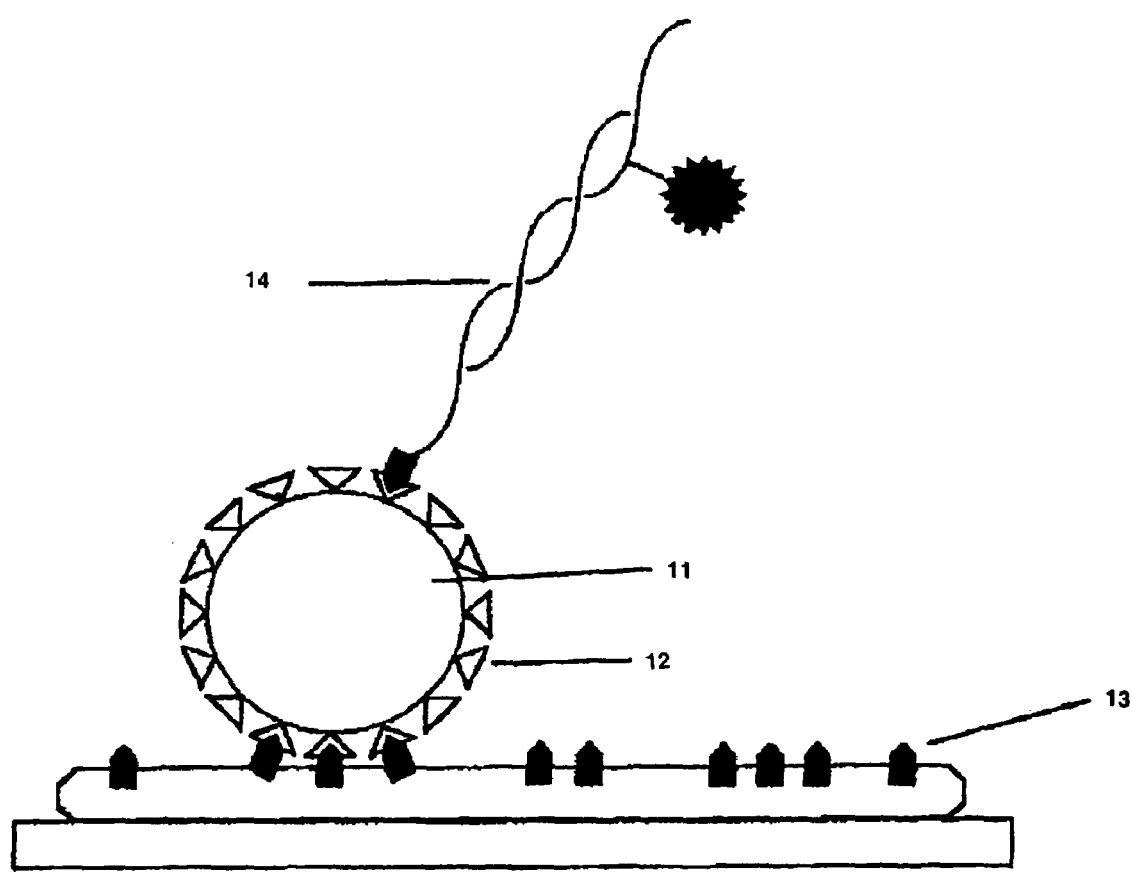
FIG. 2 illustrates the immobilisation of a polynucleotide to a solid surface via a microsphere.

In an embodiment of the invention, the target molecules are immobilised onto non-fluorescent streptavidin or avidin-functionalised polystyrene latex microspheres, as shown in FIG. 2. FIG. 2 shows a microsphere 11, a streptavidin molecule 12, a biotin molecule 13 and a fluorescently labelled polynucleotide 14. The microspheres are immobilised in turn onto a solid support to fix the target sample for microscope analysis. Alternative microspheres suitable for use in the present invention are well known in the art.

In one aspect of the present invention, the devices comprise arrayed polynucleotides, each polynucleotide comprising a hairpin loop structure, one end of which comprises a target polynucleotide, the other end comprising a relatively short polynucleotide capable of acting as a primer in the polymerase reaction. This ensures that the primer is able to perform its priming function during a polymerase-based sequencing procedure, and is not removed during any washing step in the procedure. The target polynucleotide is capable of being interrogated.

The term "hairpin loop structure" refers to a molecular stem and loop structure formed from the hybridisation of complementary polynucleotides that are covalently linked. The stem comprises the hybridised polynucleotides and the loop is the region that covalently links the two complementary polynucleotides. Anything from a 10 to 20 (or more) base pair double-stranded (duplex) region may be used to form the stem. In one embodiment, the structure may be formed from a single-stranded polynucleotide having complementary regions. The loop in this embodiment may be anything from 2 or more non-hybridised nucleotides. In a second embodiment, the structure is formed from two separate polynucleotides with complementary regions, the two polynucleotides being linked (and the loop being at least partially formed) by a linker moiety. The linker moiety forms a covalent attachment between the ends of the two polynucleotides. Linker moieties suitable for use in this embodiment will be apparent to the skilled person. For example, the linker moiety may be polyethylene glycol (PEG).

There are many different ways of forming the hairpin structure to incorporate the target polynucleotide. However, a preferred method is to form a first molecule capable of forming a hairpin structure, and ligate the target polynucleotide to this. Ligation may be carried out either prior to or after immobilisation to the solid support. The resulting structure comprises the single-stranded target polynucleotide at one end of the hairpin and a primer polynucleotide at the other end.

In one embodiment, the target polynucleotide is genomic DNA purified using conventional methods. The genomic DNA may be PCR-amplified or used directly to generate fragments of DNA using either restriction endonucleases, other suitable enzymes, a mechanical form of fragmentation or a non-enzymatic chemical fragmentation method. In the case of fragments generated by restriction endonucleases, hairpin structures bearing a complementary restriction site at the end of the first hairpin may be used, and selective ligation of one strand of the DNA sample fragments may be achieved by one of two methods.

Method 1 uses a first hairpin whose restriction site contains a phosphorylated 5' end. Using this method, it may be necessary to first de-phosphorylate the restriction-cleaved genomic or other DNA fragments prior to ligation such that only one sample strand is covalently ligated to the hairpin.

Method 2, in the design of the hairpin, a single (or more) base gap can be incorporated at the 3' end (the receded strand) such that upon ligation of the DNA fragments only one strand is covalently joined to the hairpin. The base gap can be formed by hybridising a further separate polynucleotide to the 5'-end of the first hairpin structure. On ligation, the DNA fragment has one strand joined to the 5'-end of the first hairpin, and the other strand joined to the 3'-end of the further polynucleotide. The further polynucleotide (and the other strand of the DNA fragment) may then be removed by disrupting hybridization.

In either case, the net result should be covalent ligation of only one strand of a DNA fragment of genomic or other DNA, to the hairpin. Such ligation reactions may be carried out in solution at optimised concentrations based an conventional ligation chemistry, for example, carried out by DNA ligases or non-enzymatic chemical ligation. Should the fragmented DNA be generated by random shearing of genomic DNA or polymerase, then the ends can be filled in with Klenow fragment to generate blunt-ended fragments which may be blunt-end-ligated onto blunt-ended hairpins. Alternatively, the blunt-ended DNA fragments may be ligated to oligonucleotide adapters which are designed to allow compatible ligation with the sticky-end hairpins, in the manner described previously.

The hairpin-ligated DNA constructs may then be covalently attached to the surface of a solid support to generate a single molecule array (SMA), or ligation may follow attachment to form the array.

The arrays may then be used in procedures to determine the sequence of the target polynucleotide. If the target fragments are generated via restriction digest of genomic DNA, the recognition sequence of the restriction or other nuclease enzyme will provide 4, 6, 8 bases or more of known sequence (dependent on the enzyme). Further sequencing of between 10 and 20 bases on the SMA should provide sufficient overall sequence information to place that stretch of DNA into unique context with a total human genome sequence, thus enabling the sequence information to be used for genotyping and more specifically single nucleotide polymorphism (SNP) scoring.

Simple calculations have suggested the following based on sequencing a $10^7$ molecule SMA prepared from hairpin ligation. For a 6 base pair recognition sequence, a single restriction enzyme will generate approximately $10^4$ ends of DNA. If a stretch of 13 bases is sequenced on the SMA (i.e $13 \times 10^6$ bases), approximately 13,000 SNPs will be detected. One application of such a sample preparation and sequencing format would in general be for SNP discovery in pharmaco-genetic analysis. The approach is therefore suitable for forensic analysis or any other system which requires umambiguous identification of individuals to a level as low $10^3$ SNPs.

It is of course possible to sequence the complete target polynucleotide, if required.

In a separate aspect of the invention, the devices may comprise immobilised polynucleotides and other immobilised molecules. The other molecules are relatively short compared to the polynucleotides and are intended to prevent non-specific attachment of reagents, e.g. fluorophores, with the solid support, thereby reducing background interference. In one embodiment, the other molecules are relatively short polynucleotides. However, many different molecules may be used, e.g. peptides, proteins, polymers and synthetic chemicals, as will be apparent to the skilled person. Preparation of the devices may be carried out by first preparing a mixture of the relatively long polynucleotides and of the relatively short molecules. Usually, the concentration of the latter will be in excess of that of the long polynucleotides. The mixture is then placed in contact with a suitably prepared solid support, to allow immobilisation to occur.

The single molecule arrays have many applications in methods which rely on the detection of biological or chemical interactions with arrayed molecules. For example, the arrays may be used to determine the properties or identities of cognate molecules. Typically, interaction of biological or chemical molecules with the arrays are carried out in solution.

In particular, the arrays may be used in conventional assays which rely on the detection of fluorescent labels to obtain information on the arrayed molecules. The arrays are particularly suitable for use in multi-step assays where the loss of synchronisation in the steps was previously regarded as a limitation to the use of arrays. When the arrays are composed of polynucleotides they may be used in conventional techniques for obtaining genetic sequence information. Many of these techniques rely on the stepwise identification of suitably labelled nucleotides, referred to in U.S. Pat. No. 5,634,413 as "single base" sequencing methods.

In an embodiment of the invention, the sequence of a target polynucleotide is determined in a similar manner to that described in U.S. Pat. No. 5,634,413, by detecting the incorporation of nucleotides into the nascent strand through the detection of a fluorescent label attached to the incorporated nucleotide. The target polynucleotide is primed with a suitable primer (or prepared as a hairpin construct which will contain the primer as part of the hairpin), and the nascent chain is extended in a stepwise manner by the polymerase reaction. Each of the different nucleotides (A, T, G and C) incorporates a unique fluorophore at the 3' position which acts as a blocking group to prevent uncontrolled polymerization. The polymerase enzyme incorporates a nucleotide into the nascent chain complementary to the target, and the blocking group prevents further incorporation of nucleotides. The array surface is then cleared of unincorporated nucleotides and each incorporated nucleotide is "read" optically by a charge-coupled detector using laser excitation and filters. The 3'-blocking group is then removed (deprotected), to expose the nascent chain for further nucleotide incorporation.

Because the array consists of distinct optically resolvable polynucleotides, each target polynucleotide will generate a series of distinct signals as the fluorescent events are detected. Details of the full sequence are then determined.

The number of cycles that can be achieved is governed principally by the yield of the deprotection cycle. If deprotection fails in one cycle, it is possible that later deprotection and continued incorporation of nucleotides can be detected during the next cycle. Because the sequencing is performed at the single molecule level, the sequencing can be carried out on different polynucleotide sequences at one time without the necessity for separation of the different sample fragments prior to sequencing. This sequencing also avoids the phasing problems associated with prior art methods.

Deprotection may be carried out by chemical, photochemical or enzymatic reactions.

A similar, and equally applicable, sequencing method is disclosed in EP-A-0640146.

Other suitable sequencing procedures will be apparent to the skilled person. In particular, the sequencing method may rely on the degradation of the arrayed polynucleotides, the degradation products being characterised to determine the sequence.

An example of a suitable degradation technique is disclosed in WO-A-95/20053, whereby bases on a polynucleotide are removed sequentially, a predetermined number at a time though the use of labeled adaptors specific for the bases, and a defined exonuclease cleavage.

A consequence of sequencing using non-destructive methods is that it is possible to form a spatially addressable away for further characterisation studies, and therefore non-destructive sequencing may be preferred. In this context, term "spatially addressable" is used herein to describe how different molecules may be identified on the basis of their position on an array.

Once sequenced, the spatially addressed arrays may be used in a variety of procedures which require the characterisation of individual molecules from heterogeneous populations.

One application is to use the arrays to characterise products synthesised in combinatorial chemistry reactions. During combinatorial synthesis reactions, it is usual for a tag or label to be incorporated onto a beaded support or reaction product for the subsequent characterisation of the product. This is adapted in the present invention by using polynucleotide molecules as the tags, each polynucleotide being specific for a particular product and using the tags to hybridise onto a spatially addressed array. Because the sequence of each arrayed polynucleotide has been determined previously, the detection of a hybridisation event on the array reveals the sequence of the complementary tag on the product. Having identified the tag, it is then possible to confirm which product this relates to. The complete process is therefore quick and simple, and the arrays may be reused for high through-put screening. Detection may be carried out by attaching a suitable label to the product, e.g. a fluorophore.

Combinatorial chemistry reactions may be used to synthesise a diverse range of different molecules, each of which may be identified using the addressed arrays of the present invention. For example, combinatorial chemistry may be used to produce therapeutic proteins or peptides that can be bound to the arrays to produce an addressed array of target proteins. The targets may then be screened for activity, and those proteins exhibiting activity may be identified by their position on the array as outlined above.

Similar principles apply to other products of combinatorial chemistry, for example the synthesis of non-polymeric molecules of m.wt<1000. Methods for generating peptides/proteins by combinatorial methods are disclosed in U.S. Pat. No. 5,643,768 and U.S. Pat. No. 5,658,754. Split-and-mix approaches may also be used, as described in Nielsen et al. J Am Chem Soc (1993) 115.9812–9813.

In an alternative approach, the products of the combinatorial chemistry reactions may comprise a second polynucleotide tag not involved in the hybridisation to the array. After formation by hybridisation, the array may be subjected to repeated polynucleotide sequencing to identify the second tag which remains free. The sequencing may be carried out as described previously.

Therefore, in this application, it is the tag that provides the spatial address on the array. The tag may then be removed from the product by, for example, a cleavable linker, to leave an untagged spatially addressed array.

A further application is to display proteins via an immobilised polysome containing trapped polynucleotides and protein in a complex, as described in U.S. Pat. Nos. 5,643,768 and 5,658,754.

In a separate embodiment of the invention, the arrays maybe used to characterise an organism. For example, an organism's genomic DNA may be screened using the arrays, to reveal discrete hybidisation patterns that are unique to an individual. This embodiment may therefore be likened to a "bar code" for each organism. The organism's genomic DNA may be first fragmented and detectably-labelled, for example with a fluorophore. The fragmented DNA is then applied to the array under hybridising conditions and any hybridisation events monitored.

Alternatively, hybridisation may be detected using an in-built fluorescence based detection system in the arrayed molecule, for example using the "molecular beacons" described in Nature Biotechnology (1996) 14.303–308.

It is possible to design the arrays so that the hybridisation pattern generated is unique to the organism and so could be used to provide valuable information on the genetic character of an individual. This may have many useful applications in forensic science. Alternatively, the methods may be carried out for the detection of mutations or allelic variants within the genomic DNA of an organism.

For genotyping, it is desirable to identify if a particular sequence is present in the genome. The smallest possible unique oligomer is a 16-mer (assuming randomness of the genome sequence), i.e. statistically there is a probability of any given 16-base sequence occurring only once in the human genome (which has $3\times10^9$ bases). There are c.$4\times10^9$ possible 16-mers which would fit within a region of 2 cm×2 cm (assuming a single copy at a density of 1 molecule per 250 nm×250 nm square). It is therefore necessary to determine only if a particular 16-mer is present or not, and so quantitative measurements are unnecessary. Identifying a mutation in a particular region and what the mutation is can be carried out using the 16-mer library. Mapping back onto the human genome would be possible using published data and would not be a problem once the entire genome has been determined. There is built-in self-check, by looking at the hybridisation to particular 16-mers so that if there is a single point mutation, this will show up in 16 different 16-mers, identifying a region of 32 bases in the genome (the mutation would occur at the top of one 16-mer and then at the second base in a related 16-mer etc). Thus, a single point mutation would result in 16 of the 16-mers not showing hybridisation and a new set of 16 showing hybridisation plus the same thing for the complementary strand. In summary, considering both strands of DNA, a single point mutation would result in 32 of the 16-mers not showing hybridisation and 32 new 16-mers showing hybridisation, i e quite large changes on the hybridisation pattern to the array.

By way of example, a sample of human genomic DNA may be restriction-digested to generate short fragments, then labelled using a fluorescently-labelled monomer and a DNA polymerase or a terminal transferase enzyme. This produces short lengths of sample DNA with a fluorophore at one end. The melted fragments may then be exposed to the array and the pixels where hybridisation occurs or not would be identified. This produces a genetic bar code for the individual with (if oligonucleotides of length 16 were used) c $4\times10^9$ binary coding elements. This would uniquely define a person's genotype for pharmagenomic applications. Since the arrays should be reusable, the same process could be repeated on a different individual.

In one embodiment of the invention, a method for determining a single nucleotide polymorphism (SNP) present in a genome comprises immobilising fragments of the genome onto the surface of a solid support to form an army as defined above, identifying nucleotides at selected positions in the genome, and comparing the results with a known consensus sequence to identify any differences between the consensus sequence and the genome. Identifying the nucleotides at selected positions in the genome may be carried out by contacting the array sequentially with each of the bases A, T, G and C, under conditions that permit the polymerase reaction to proceed, and monitoring the incorporation of a base at selected positions in the complementary sequence.

The fragments of the genome may be unamplified DNA obtained from several cells from an individual, which is treated with a restriction enzyme. As indicated above, it is not necessary to determine the sequence of the full fragment. For example, it may be preferable to determine the sequence of 16–30 specific bases, which is sufficient to identify the DNA fragment by comparison to a consensus sequence, e.g. to that known from the Human Genome Project. Any SNP occurring within the sequenced region can then be identified. The specific bases do not have to be contiguous. For example, the procedure may be carried out by the incorporation of non-labelled bases followed, at pre-determined positions, by the incorporation of a labeled base. Provided that the sequence of sufficient bases is determined, it should be possible to identify the fragment. Again, any SNPs occurring at the determined base positions, can be identified. For example, the method may be used to identify SNPs that occur after cytosine. Template DNA (genomic fragments) can be contacted with each of the bases A, T and G, added sequentially or together, so that the complementary strand is extended up to a position that requires C. Non-incorporated bases can then be removed from the array, followed by the addition of C. The addition of C is followed by monitoring the next base incorporation (using a labelled base). By repeating this process a sufficient number of times, a partial sequence is generated where each base immediately following a C is known. It will then be possible to identify the full sequence by comparison of the partial sequence to a reference sequence. It will then also be possible to determine whether there are any SNPs occurring after any C.

To further illustrate this, a device may comprise $10^7$ restriction fragments per cm$^2$. If 30 bases are determined for each fragment, this means $3\times10^8$ bases are identified. Statistically, this should determine $3\times10^5$ SNPs for the experiment. If the fragments each comprise 1000 nucleotides, it is possible to have $10^{10}$ nucleotides per cm$^2$, or three copies of the human genome. The approach therefore permits large sequence or SNP analysis to be performed.

Viral and bacterial organisms may also be studied, and screening nucleic acid samples may reveal pathogens present in a disease, or identify microorganisms in analytical techniques. For example, pathogenic or other bacteria may be identified using a series of single molecule DNA chips produced from different strains of bacteria. Again, these chips are simple to make and reusable.

In a further example, double-stranded arrays may be used to screen protein libraries for binding, using fluorescently labelled proteins. This may determine proteins that bind to a particular DNA sequence, i e proteins that control transcription. Once the short sequence that the protein binds to has been determined, it may be made and affinity purification used to isolate and identify the protein. Such a method could find all the transcription-controlling proteins. One such method is disclosed in Nature Biotechnology (1999) 17.573–577.

Another use is in expression monitoring. For this, a label is required for each gene. There are approximately 100,000 genes in the human genome. There are 262,144 possible 9-mers, so this is the minimum length of oligomer needed to have a unique tag for each gene. This 9-mer label needs to be at a specific point in the DNA and the best point is probably immediately after the poly-A tail in the mRNA (i e a 9-mer linked to a poly-T guide sequence). Multiple copies of these 9-mers should be present, to permit quantitation of gene expression. 100 copies would allow determination of relative expression from 1–100%. 10,000 copies would allow determination of relative gene expression from 0.01–100%. 10,000 copies of 262,144 9-mers would fit inside 1 cm×1 cm at close to maximum density.

The use of nanovials in conjunction with any of the above methods may allow a molecule to be cleaved from the surface, yet retain its spatial integrity. This permits the generation of spatially addressable arrays of single molecules in free solution, which may have advantages where the surface attachment impedes the analysis (e.g drug screening). A nanovial is a small cavity in a flat glass surface, e.g. approx 20 µm in diameter and 10 µm deep. They can be placed every 50 µm, and so the array would be less dense than a surface-attached array; however, this could be compensated for by appropriate adjustment in the imaging optics.

The following Examples illustrate the invention, with reference to the accompanying drawings.

EXAMPLE 1

The microscope set-up used in the following Example was based on a modified confocal fluorescence system using a photon detector as shown in FIG. 1. Briefly, a narrow, spatially filtered laser beam (CW Argon ton Laser Technology RPC50) was passed through an acousto-optic modulator (AOM) (A A Opto-Electronic) which acts as a fast optical switch. The acousto-optic modulator was switched on and, the laser beam was directed through an oil emersion objective (100×NA=1 3) of an inverted optical microscope (Nikon Diaphor 200) by a dichroic beam splitter (540DRLP02 or 505DRLP02, Omega Optics Inc). The objective focuses the light to a diffraction-limited spot on the target sample immobilised on a thin glass coverslip. Fluorescence from the sample was collected by the same objective, passed through the dichroic beam splitter and directed though a 50 µm pinhole (Newport Corp.) placed in the image plane of the microscope observation port. The pinhole rejects light emerging from the sample which is out of the plane of the laser scatter. The remaining fluorescence was separated spectrally by a dichroic beam splitter into red and green components which was filtered to remove residual laser scatter. The remaining fluorescence components were then focused onto separate single photon avalanche diode detectors and the signals recorded onto a multichannel scalar (MCS) (MCS-Plus, E G & G Ortec) with time resolutions in the 1 to 10 ms range.

The target sample was a 5'-biotin-modified 13-mer primer oligonucleotide prepared using conventional phosphoramidite chemistry, and having SEQ ID No 1 (see listing, below). The oligonucleotide was post-synthetically modified by reaction of the uridine base with the succinimdyl ester of tetramethylrhodamine (TMR).

Glass coverslips were prepared by cleaning with acetone and drying under nitrogen. A 50 µl aliquot of biotin-BSA (Sigma) redissolved in PBS buffer (0.01 M, pH 7.4) at 1 mg/ml concentration was deposited on the clean coverslip and incubated for 8 hours at 30° C. Excess biotin-BSA was removed by washing 5 times with MilliQ water and drying under nitrogen. Non-fluorescent streptavidin functionalised polystyrene latex microspheres of diameter 500 nm (Polysciences Inc) were diluted in 100 mM NaCl to 0 1 solids and deposited as a 1 µl drop on the biotinylated coverslip surface. The spheres were allowed to dry for one hour and unbound beads removed by washing 5 times with MilliQ water. This procedure resulted in a surface coverage of approximately 1 sphere/100 µm×100 µm.

The non-fluorescent microspheres were found to have a broad residual fluorescence at excitation wavelength 514 nm, probably arising from small quantities of photoactive constituents used in the colloidal preparation of the microspheres. The microspheres were therefore photobleached by treating the prepared coverslip in a laser beam of a frequency doubled (532 nm) Nd.YAG pulsed dye laser, for 1 hour.

The biotinylated I3-TMR ssDNA was coupled to the streptavidin functionalised microspheres by incubating a 50 µl sample of 0.1 pM DNA (diluted in 100 mM NaCl, 100 mM Tris) deposited over the microspheres. Unbound PNA was removed by washing the coverslip surface 5 times with MilliQ water.

Low light level illumination from the microscope condenser was used to position visually a microsphere at 10× magnification so that when the laser was switched on the sphere was located in the centre of the diffraction limited focus. The condenser was then turned off and the light path switched to the fluorescence detection port. The MCS was initiated and the fluorescence omitted from the latex sphere recorded on one or both channels. The sample was excited at 514 nm and detection was made on the 600 nm channel.

Figure 3:
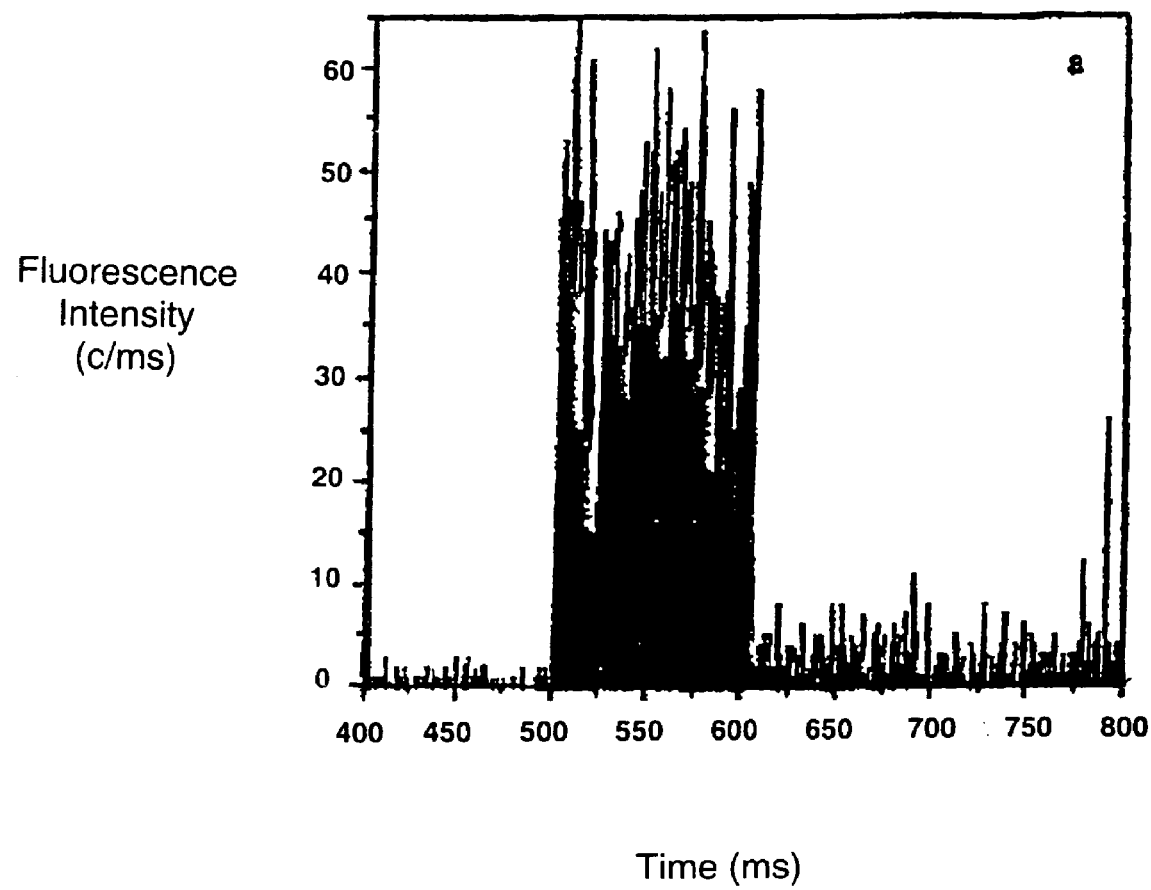
FIG. 3 shows a fluorescence time profile from a single fluorophore-labelled oligonucleotide, with excitation at 514 nm and detection at 600 nm.

FIG. 3 shows clearly that the fluorescence is switched on as the laser is deflected into the microscope by the AOM, 0 5 seconds after the start of a scan. The intensity of the fluorescence remains relatively constant for a short period of time (100 ms–3s) and disappears in a single step process. The results show that single molecule detection is occurring. This single step photobleaching is unambiguous evidence that the fluorescence is from a single molecule.

EXAMPLE 2

This Example illustrates the preparation of single molecule arrays by direct covalent attachment to glass followed by a demonstration of hybridisation to the array.

Covalently modified slides were prepared as follows. Spectrosil-2000 slides (TSL, UK) were rinsed in milli-Q to remove any dust and placed wet in a bottle containing near Decon-90 and left for 12 h at room temperature. The slides were rinsed with milli-Q and placed in a bottle containing a solution of 1.5% glycidoxypropyltrimethoxy-silane in milli-Q and magnetically stirred for 4 h at room temperature rinsed with milli-Q and dried under $N_2$ to liberate an epoxide coated surface.

The DNA used was that shown in SEQ ID No. 2 (see sequence listing below), where n represents a 5-methyl cytosine (Cy5) with a TMR group coupled via a link to the n4 position.

A sample of this (5 µl, 450 pM) was applied as a solution in neat milli-Q.

The DNA reaction was left for 12 h at room temperature in a humid atmosphere to couple to the epoxide surface. The slide was then rinsed with milli-Q and dried under $N_2$.

The prepared slides can be stored wrapped in foil in a desiccator for at least a week without any noticeable contamination or loss of bound material. Control DNA of the same sequences and fluorophore but without the 5'-amino group shows little stable coverage when applied at the same concentration.

The TMR labelled slides were then treated with a solution of complementary DNA (SEQ D No. 3) (5 µM, 10 µl) in 100 nM PBS. The complementary DNA has the sequence shown in SEQ ID No. 3, where n represents a methylcytosine group.

After 1 hour at room temperature the slides were cooled to 4° C. and left for 24 hours. Finally, the slides were washed in PBS (100 mM, 1 mL) and dried under $N_2$.

A chamber was constructed on the slide by sealing a coverslip (No 0, 22×22 mm, Chance Propper Ltd, UK) over the sample area on two sides only with prehardened microscope mounting medium (Eukitt, O. Kindler GmbH & Co Freiburg, Germany) whilst maintaining a gap of less than 200 µm between slide and coverslip. The chamber was flushed 3× with 100 µl PBS (100M NaCl) and allowed to stabilise for 5 minutes before analysing on a fluorescence microscope.

The slide was inverted so that the chamber coverslip contacted the objective lens of an inverted microscope (Nikon TE200) via an immersion oil interface. A 60° fused silica dispersion prism was optically coupled to the back of the slide through a thin film of glycerol. Laser light was directed at the prism such that at the glass/sample interface it subtends an angle of approximately 68° to the normal of the slide and subsequently undergoes total Internal Reflection (TIR). The critical angle for water interface is 66°.

Fluorescence from single molecules of DNA-TMR or DNA-Cy5 produced by excitation with the surface specific evanescent wave following TIR is collected by the objective lens of the microscope and imaged onto an intensified Charge Coupled Device (ICCD) camera (Pentamax, Princeton Instruments, N.J.). Two images were recorded using a combination of 1) 532 nm excitation (frequency doubled solid state Nd YAG, Antares, Coherent) with a 580 nm fluorescence (580DF30, Omega Optics, USA) filter for TMR and 2) 630 nm excitation (nd-YAG pumped dye laser, Coherent 700) with a 670 nm filter (670DF40, Omega Optics, USA) for Cy5. Images were recorded with an exposure time of 500 ms at the maximum gain of 10 on the ICCD. Laser powers incident at the prism were 50 mW and 40 mW at 532 nm and 630 nm respectively. A third image was taken with 532 nm excitation and detection at 670 nm to determine the level of cross talk from TMR on the Cy5 channel.

Single molecules were identified by single points of fluorescence with average intensities greater than 3× that of the background. Fluorescence from a single molecule is confined to a few pixels typically a 3×3 matrix at 100× magnification, and has a narrow Gaussian-like intensity profile. Single molecule fluorescence is also characterised by a one-step photobleaching process in the time course of the intensity and was used to distinguish single molecules from pixel regions containing two or more molecules, which exhibited multi-step processes. FIGS. 4a and 4b show 60 µm×60 µm fluorescence images from covalently modified slides with DNA-TMR starting concentrations of 45 pM and 450 pM. FIG. 4c shows a control slide which was treated as above but with DNA-TMR lacking the 5' amino modification.

To count molecules, a threshold for fluorescence intensities is first set to exclude background noise. For a control sample, the background is essentially the thermal noise of the ICCD measured to be 76 counts with a standard deviation of only 6 counts. A threshold is arbitrarily chosen as a linear combination of the background, the average counts over an image and the standard deviation over an image. In general, the latter two quantities provide a measure of the number of pixels and range of intensities above background. This method gives rise to threshold levels which are at least 12 standard deviations above the background with a probability of less than 1 in 144 pixels contributing from noise. By defining a single molecule fluorescent point as being at least a 2×2 matrix of pixels and no larger than a 7×7, the probability of a single background pixel contributing to the counting is eliminated and clusters are ignored.

In this manner, the surface density of single molecules of DNA-TMR is measured at $2.9 \times 10^6$ molecules/cm$^2$ (238 molecules in FIG. 4a) and 5 $8 \times 10^6$ molecules/cm$^2$ (469 molecules in FIG. 4b) at 45 pM and 450 pM DNA-TMR coupling concentrations. The density is clearly not directly proportional to DNA concentration but will be some function of the concentration, the volume of sample applied, the area covered by the sample and the incubation time. The percentage of non-specifically bound DNA-TMR and impurities contribute of the order of 3–9% per image (8 non-specifically bound molecules in FIG. 4c). Analysis of the photobleaching profiles shows only 6% of fluorescence points contain more than 1 molecule.

Hybridisation was identified by the co-localisation of discreet points of fluorescence from single molecules of TMR and Cy-5 following the superposition of two images. FIGS. 5a and 5b show images of surface bound 20-mer labelled with TMR and the complementary 20-mer labelled with Cy-5 deposited from solution. FIG. 5d shows those fluorescent points that are co-localised on the two former images. The degree of hybridisation was estimated to be 7% of the surface-bound DNA (10 co-localised points in 141 points from FIGS. 5d and 5a, respectively). The percentage of hybridised DNA is estimated to be 37% of all surface-adsorbed DNA-Cy5 (10 co-localised points in 27 points from FIGS. 5d and 5b, respectively). Single molecules were counted by matching size and intensity of fluorescent points to threshold criteria which separate single molecules from background noise and cosmic rays. FIG. 5d shows the level of cross-talk from TMR on the Cy5 channel which is 2% as determined by counting only those fluorescent points which fall within the criteria for determining the TMR single molecule fluorescence (2 fluorescence points in 141 points from FIGS. 5c and 5a, respectively).

This Example demonstrates that single molecule arrays can be formed, and hybridisation events detected according to the invention. It is expected that the skilled person will realise that modifications may be made to improve the efficiency of the process. For example, improved washing steps, e g using a flow cell, would reduce background noise and permit more concentrated solutions to be used, and hybridisation protocols could be adapted by varying the parameters of temperature, buffer, time etc.

EXAMPLE 3

This experiment demonstrates the possibility of performing enzymatic incorporation on a single molecule array. In summary, primer DNA was attached to the surface of a solid support, and template DNA hybridised thereto. Two cycles of incorporation of fluorophore-labelled nucleotides was then completed. This was compared against a reference experiment where the immobilised DNA was pre-labelled with the same two fluorophores prior to attachment to the surface, and control experiments performed under adverse conditions for nucleotide incorporation.

The primer DNA sequence and the template DNA sequence used in this experiment are shown in SEQ ID NOS. 4 and 5, respectively.

The buffer used contained 4 mM MgCl$_2$, 2 mM DTT, 50 mM Tris HCl (pH 7 6) 10 mM NaCl and 1 mm K$_2$PO$_3$ (100 µl).

Preparation of Slides.

Silica slides were treated with decon for at least 24 hours and rinsed in water and EtOH directly before use. The dried slides were placed in a 50 ml solution of 2% glycidoxypropyltrimethoxysalane in EtOH/H$_2$SO$_4$ (2 drops/500 ml) at room temperature for 2 hours. The slides were then rinsed in EtOH from a spray bottle and dried under N$_2$. The DNA samples (SEQ to NO 4) were applied either as a 40–100 pM solution (5 µl) in 10 mM K$_2$PO$_3$ pH 7.6 (allowed to dry overnight), or at least 1 µM concentration over a sealed slide. The slides allowed to dry overnight were left over a layer of water for 18 hours at room temperature and then rinsed with milli-q (approx. 30 ml from a spray bottle) and dried under $N_2$. The sealed slides were simply flushed with 50 ml buffer prior to use. Control slides with no coupled DNA were simply left under the buffer for identical time periods.

Enzyme Extensions on a Surface.

For the first incorporation cycle, samples were prepared with the buffer containing BSA (to 0.2 mg/ml), the triphosphate (Cy3dUTP; to 20 µM) and the polymerase enzyme (T4 exo-; to 500 nM). In certain experiments, the template DNA was also added at 2 µM. The mixture was flowed into cells which were incubated at 37° C. for 2 hours and flushed with 500 ml buffer. The second incorporation cycle with Cy5dCTP (20 µM), dATP (100 µm) and dGTP (100 µM) was performed in the same way. The cells were flushed with 50 ml buffer and left for 12 hours prior to imaging. Control reactions were performed as above with a) no DNA coupled prior to extension; b) DNA attached but no polymerase in the extension buffer, and c) DNA attached, but the polymerase denatured by boiling.

Reference Sample.

A reference sample, not immobilised to the surface, was prepared in the following way.

Buffer containing 1 µM of the sample DNA, BSA (0.2 mg/ml), TMR-labelled dUTP (20 µM) and the polymerase enzyme (T4 exo-, 500 nM; 100 µl) was prepared. The reaction was analysed and purified by reverse phase HPLC (5–30% acetonitrile in ammonium acetate over 30 min.) with UV and fluorescence detection in all cases, the labelled DNA was clearly separate from both the unlabelled DNA and the labelled dNTP's. The material was concentrated and dissolved in 10 mM $K_2PO_3$ for analysis by A260 and fluorescence. The material purified by HPLC was further extended with labelled dCTP (20 µM), dATP (100 µM) and dGTP (100 µM) and HPLC purified again. Surface coupling was then performed dry, at 100 µM concentrations.

Microscopic Analysis.

Following the single molecule DNA attachment procedure and extension reactions, the sample cells were analysed on a single molecule total internal reflection fluorescence microscope (TIRFM in the following manner. A 60° fused silica dispersion prism was coupled optically to the slide through an aperture in the cell via a thin film of glycerol. Laser light was directed at the prism such that at the glass/sample interface it subtends an angle of approximately 68° to the normal of the slide and subsequently undergoes total internal reflection. The critical angle for a glass/water interface is 66°. An evanescent field is generated at the interface which penetrates only ~150 nm into the aqueous phase. Fluorescence from single molecules excited within this evanescent field is collected by a 100× objective lens of an inverted microscope, filtered spectrally from the laser light and imaged onto an Intensified Charge Coupled Device (ICCD) camera.

Two 90 µm×90 µm images were recorded using a combination of: 1) 532 nm excitation (frequently doubled Nd.YAG) with a 580 nm interference filter for Cy5 detection, and 2) 630 nm excitation (Nd.YAG pumped DCM dye laser) with a 670 nm filter for Cy5 detection. Images were recorded with an exposure time of 500 ms at the maximum ICCD gain of 5.75 counts/photoelectron. Laser powers incident at the prism were 30 mW and 30 mW at 532 nm and 630 nm respectively. Two colour fluorophore labelled nucleotide incorporations are identified by the co-localisation of discrete points of fluorescence from single molecules of Cy3 and Cy5 following superimposing the two images. Molecules are considered co-localised when fluorescent points are within a pixel separation of each other. For a 90 µm×90 µm field, projected onto a CCD array of 512×512 pixels, the pixel size dimension is 0 176 µm.

Results. The results of the experiment are shown in Table 1. The values shown are an average of the number of molecules imaged (Cy3 and Cy5) over all frames (100 in each) compiled in each experiment and the number of those molecules which are co-localised.

The final column represents the number of co-localised molecules expected if the two fluorophores were randomly dispersed across the sample slide ($N \sim \pi \Delta \gamma$ where n is the surface density of molecules and $\Delta \gamma = 0$ 176 µm is the minimum measurable separation). The number in brackets indicates the magnitude by which the level of co-locations in each experiment is greater than random.

TABLE 1

| System | Cy3 | Cy5 | Co-local | % of Total | Random |
|---|---|---|---|---|---|
| Reference | 30 | 36 | 3 | 8 | 0.05 (×100) |
| Incorporation A | 75 | 75 | 12 | 8 | 0.3 (×40) |
| Incorporation B | 354 | 570 | 76 | 8 | 10 (×7.6) |
| No DNA | 100 | 280 | 9 | 2 | 2 (×3.5) |
| No Enzyme | 26 | 332 | 3 | 1 | 1/5 (×2) |
| Denatured T4 | 89 | 624 | 18 | 2.5 | 6 (×3) |

The percentage of co-localisation observed on this sample represents the maximum measurable for a dual labelled system, i.e. there is a detection ceiling due to photophysical effects which means the level is not 100%. These effects may arise from interactions of the fluorophores with the DNA or the surface or both.

There is a statistically higher level of co-localisation in the incorporation experiments compared to the controls (8% versus 2% respectively). This shows that it is possible to perform enzymatic incorporation on the SMA and the level of incorporation is close to that of the reference sequence. Improvements in the surface attachment and the nature of the surface are required to increase the level of co-localisation in the reference and to increase the detection efficiency of the enzyme incorporation.

EXAMPLE 4

This Example illustrates the preparation of single molecule arrays by direct covalent attachment of hairpin loop structures to glass.

A solution of 1% glycidoxypropyltrimethoxy-silane in 95% ethanol/5% water with 2 drops $H_2SO_4$ per 500 ml was stirred for 5 minutes at room temperature. Clean, dry Spectrosil-2000 slides (TSL, UK) were placed in the solution and the stirring stopped. After 1 hour the slides were removed, rinsed with ethanol, dried under $N_2$ and oven-cured for 30 min at 100° C. These 'epoxide' modified slides were then treated with 1 µM of labelled DNA (5'-Cy3-CTGCT-GAAGCGTCGGCAGGT-heg-ami-nodT-heg-ACCTGC-CGACGCT-3') (SEQ ID NOS. 6 and 7) in 50 mM potassium phosphate buffer, pH 7.4 for 18 hours at room temperature and, prior to analysis, flushed with 50 mM potassium phosphate, 1 mM EDTA, pH 7.4. The coupling reactions were performed in sealed teflon blocks under a pre-mounted coverslip to prevent evaporation of the sample and allow direct imaging.

The DNA structure was designed as a self-priming template system with an internal amino group attached as an amino deoxy-thymidine held by two 18 atom hexaethylene glycol (heg) spacers, and was synthesised by conventional DNA synthesis techniques using phosphoramidite monomers.

For imaging, one slide was inverted so that the chamber coverslip contacted the objective lens of an inverted microscope (Nikon TE200) via an immersion oil interface. A 60° C. fused silica dispersion prism was coupled optically to the back of the slide through a thin film of glycerol. Laser light was directed at the prism such that at the glass/sample interface it subtends an angle of approximately 68° C. to the normal of the slide and subsequently undergoes Total Internal Reflection (TIR). The critical angle for glass/water interface is 66°.

Fluorescence from single molecules of DNA-Cy3, produced by excitation with the surface-specific evanescent wave following TIR, was collected by the objective lens of the microscope and imaged onto an Intensified Charge Coupled Device (ICCD) camera (Pentamax, Princeton Instruments, N.J.). The image was recorded using a 532 nm excitation (frequency-doubled solid-state Nd.YAG, Antares, Coherent) with a 580 nm fluorescence (580DF30, Omega Optics, USA) filter for Cy3. Images were recorded with an exposure time of 500 ms at the maximum gain of 10 an the ICCD. Laser powers incident at the prism were 50 mW at 532 nm.

Single molecules were identified as described in Example 2.

The surface density of single molecules of DNA-Cy3 was measured at approximately 500 per 100 μm×100 μm image or $5 \times 10^6$ cm$^2$.

What is claimed is:

1. A method for analysing genome wide variation in an individual comprising:
   i) randomly fragmenting a genome of said individual;
   ii) generating sequence reads of multiple bases on all fragments of said genome;
   iii) aligning the sequence reads with a known genomic reference sequence; and
   iv) analysing variations between the sequence reads derived from the genome of the individual and the known genomic reference sequence.

2. A method according to claim 1 further comprising identifying regions of variation across the whole of the genome of said individual with respect to said reference sequence to provide a genetic signature for said individual.

3. A method according to claim 1, wherein said fragments of genomic DNA are immobilised onto the surface of a solid support to form an array of polynucleotide molecules capable of interrogation and which molecules can be individually resolved by optical microscopy.

4. A method according to claim 1, wherein each molecule is immobilised by covalent attachment to the surface of said solid support other than at that part of each molecule that can be interrogated.

5. A method according to claim 4, wherein the sequences of said fragments are established by contacting the array with each of the bases A, T G and C under conditions that permit the polymerase reaction to proceed and thereby form sequences complementary to those in the array, and determining the incorporation of a base at each of selected positions in the complementary sequences.

6. A method according to claim 5, wherein the determination of the incorporation of said base is repeated between 10 and 20 times to generate a partial complementary sequence of between 10–20 nucleotides.

7. A method for analysing genome wide variation in an individual comprising:
   i) randomly fragmenting a genome of said individual;
   ii) arraying the fragments such that different fragments can be individually resolved by optical microscopy;
   iii) generating sequence reads of multiple bases on all fragments of said genome;
   iv) aligning said sequence reads with a known genomic reference sequence; and
   v) analysing variations between the sequence reads derived from the individual sample and the known genomic reference sequence.

8. A method of generating a genetic signature for an individual, which method comprises:
   i) immobilising fragments of the genome of said individual onto the surface of a solid support to form an array of polynucleotide molecules capable of interrogation, wherein the array allows the molecules to be individually resolved by optical microscopy, and wherein each molecule is immobilised by covalent bonding to the surface, other than at that part of each molecule that can be interrogated;
   ii) contacting the fragments with a series of nucleotide primers comprising sequences capable of hybridising to regions on said fragments specific for each of the regions of variation identified according to claim 2, in the presence of bases A, T, G and C under conditions that permit the polymerase reaction to proceed;
   iii) determining the successive incorporation of a base at each of selected positions to produce sequences of a defined length complementary to the immobilised fragments;
   iv) identifying the sequence of those fragments that have undergone the polymerase reaction to produce a genetic signature for said individual.

9. A method according to claim 7 or 8, wherein in step iii) the incorporation of said base is repeated between 10 and 20 times to produce a complementary sequence of between 10 and 20 nucleotides.

* * * * *

UNITED STATES PATENT AND TRADEMARK OFFICE
CERTIFICATE OF CORRECTION

PATENT NO. : 7,232,656 B2  Page 1 of 1
APPLICATION NO. : 10/610305
DATED : June 19, 2007
INVENTOR(S) : Shankar Balasubramanian et al.

It is certified that error appears in the above-identified patent and that said Letters Patent is hereby corrected as shown below:

Title Page; item (75); should read;
Inventors:    Shankar Balasubramanian, Saffron Walden David Klenerman, Saffron Walden Colin Barnes, Saffron Walden Mark Allen Osborne, Saffron Walden Signed and Sealed this Eleventh Day of September, 2007

JON W. DUDAS
*Director of the United States Patent and Trademark Office*

ми

(12) INTER PARTES REEXAMINATION CERTIFICATE (1078th)
United States Patent
Balasubramanian et al.

(10) Number: US 7,232,656 C1
(45) Certificate Issued: *Mar. 27, 2015

(54) ARRAYED BIOMOLECULES AND THEIR USE IN SEQUENCING

(75) Inventors: Shankar Balasubramanian, Saffron Walden (GB); David Klenerman, Saffron Walden (GB); Colin Barnes, Saffron Walden (GB); Mark Allen Osborne, Saffron Walden (GB)

(73) Assignee: Solexa Ltd., Little Chesterford, Saffron Walden, Essex (GB)

Reexamination Request:
No. 95/000,528, Mar. 5, 2010

Reexamination Certificate for:
Patent No.: 7,232,656
Issued: Jun. 19, 2007
Appl. No.: 10/610,305
Filed: Jun. 30, 2003

Certificate of Correction issued Sep. 11, 2007

(*) Notice: This patent is subject to a terminal disclaimer.

Related U.S. Application Data

(63) Continuation of application No. 09/771,708, filed on Jan. 30, 2001, now Pat. No. 6,787,308, which is a continuation-in-part of application No. PCT/GB99/02487, filed on Jul. 30, 1999.

(30) Foreign Application Priority Data

Jul. 30, 1998 (EP) ..................................... 98306094
Oct. 16, 1998 (GB) ..................................... 9822670.7
Feb. 1, 2000 (GB) ..................................... 0002310.1

(51) Int. Cl.
| | |
|---|---|
| C12Q 1/68 | (2006.01) |
| C07H 21/02 | (2006.01) |
| C07H 21/04 | (2006.01) |
| B01J 19/00 | (2006.01) |

(52) U.S. Cl.
CPC ........... *B01J 19/0046* (2013.01); *C12Q 1/6837* (2013.01)
USPC ............. 506/9; 435/6.12; 536/23.1; 536/24.3

(58) Field of Classification Search
None
See application file for complete search history.

(56) References Cited

To view the complete listing of prior art documents cited during the proceeding for Reexamination Control Number 95/000,528, please refer to the USPTO's public Patent Application Information Retrieval (PAIR) system under the Display References tab.

*Primary Examiner* — Shri Ponnaluri

(57) ABSTRACT

The invention is directed to a method for analysing genome wide variation in an individual. The method comprises randomly fragmenting the individual's genome and generating sequence reads of multiple bases on all fragments of the individual's genome, aligning the sequence reads generated with a known genomic reference sequence, and analysing variations between the sequence reads derived from the individual's genome and the known genomic reference sequence.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-9 are cancelled.

\* \* \* \* \*

```
                          SEQUENCE LISTING

<160> NUMBER OF SEQ ID NOS: 7

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: misc_feature
<222> LOCATION: (1)..(13)
<223> OTHER INFORMATION: Modified base.  n = 5'-(propargylamino)uridine

<400> SEQUENCE: 1
tcgcagccgn cca                                                        13

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: misc_feature
<222> LOCATION: (1)..(21)
<223> OTHER INFORMATION: Modified base.  n = 5-methyl cytosine with a
      TMR group coupled via a linker to the n4 position.

<400> SEQUENCE: 2
aaccctatgg acggctgcga n                                               21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: misc_feature
<222> LOCATION: (1)..(21)
<223> OTHER INFORMATION: Modified base.  n = methyl cytosine.

<400> SEQUENCE: 3
ntcgcagccg tccatagggt t                                               21

<210> SEQ ID NO 4
<211> LENGTH: 40
<212> TYPE: DNA
<213> ORGANISM: Artificial Sequence
<220> FEATURE:
```

```
<223> OTHER INFORMATION: Description of Artificial Sequence:
      Oligonucleotide
<220> FEATURE:
<221> NAME/KEY: misc_feature
<222> LOCATION: (1)..(40)
<223> OTHER INFORMATION: Modified base.  N = (C6-amino)adenine

<400> SEQUENCE: 4
nctcaaccaa cctgccgacg ctccgagctg caagctactg                              40

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
tcgactgctg acagtagctt gcagctcgga gcgtcggcag gttggttgag t                 51

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide
<220> FEATURE:
<221> NAME/KEY: misc_feature
<222> LOCATION: (1)..(20)
<223> OTHER INFORMATION: Modified base.  N = cytosine with a fluorescent
      Cy3 group attached.  M = thymine with hexaethylene
      glycol attached.

<400> SEQUENCE: 6
ctgctgaagc gtcggcaggt                                                    20

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence:
      Oligonucleotide
<220> FEATURE:
<221> NAME/KEY: misc_feature
<222> LOCATION: (1)..(13)
<223> OTHER INFORMATION: Modified base.  N = adenine with hexaethylene
      glycol attached.

<400> SEQUENCE: 7
acctgccgac gct                                                           13
```